(12) United States Patent
Meyer (10) Patent No.: US 9,066,865 B2
(45) Date of Patent: Jun. 30, 2015

(54) PHARMACEUTICAL COMPOSITIONS FOR THE TREATMENT OF INNER EAR DISORDERS

(71) Applicant: AURIS MEDICAL AG, Basel (CH)

(72) Inventor: Thomas Meyer, Zuchwil (CH)

(73) Assignee: AURIS MEDICAL AG, Basel (CH)

( * ) Notice: Subject to any disclaimer, the term of this patent is extended or adjusted under 35 U.S.C. 154(b) by 0 days.

(21) Appl. No.: 14/317,319

(22) Filed: Jun. 27, 2014

(65) Prior Publication Data

US 2014/0364836 A1    Dec. 11, 2014

Related U.S. Application Data

(63) Continuation of application No. 11/992,632, filed as application No. PCT/EP2005/010478 on Sep. 28, 2005.

(51) Int. Cl.

| | |
|---|---|
| *A61K 9/10* | (2006.01) |
| *A61M 31/00* | (2006.01) |
| *A61K 31/137* | (2006.01) |
| *A61K 9/00* | (2006.01) |
| *A61K 31/136* | (2006.01) |
| *A61K 31/4535* | (2006.01) |
| *A61K 45/06* | (2006.01) |
| *A61K 47/34* | (2006.01) |

(52) U.S. Cl.
CPC ............... *A61K 9/10* (2013.01); *A61K 9/0046* (2013.01); *A61K 31/137* (2013.01); *A61K 31/136* (2013.01); *A61K 31/4535* (2013.01); *A61K 45/06* (2013.01); *A61K 47/34* (2013.01); *A61M 31/00* (2013.01)

(58) Field of Classification Search
CPC ........ A61K 9/10; A61K 31/137; A61M 31/00
See application file for complete search history.

(56) References Cited

U.S. PATENT DOCUMENTS

| | | |
|---|---|---|
| 3,254,124 A | 5/1966 | Stevens |
| 5,421,818 A | 6/1995 | Arenberg |
| 5,474,529 A | 12/1995 | Arenberg |
| 5,476,446 A | 12/1995 | Arenberg |
| 5,654,337 A | 8/1997 | Roentsch et al. |
| 5,716,961 A | 2/1998 | Sands |

(Continued)

FOREIGN PATENT DOCUMENTS

| | | |
|---|---|---|
| CA | 2548892 A1 | 6/2005 |
| DE | 2062620 | 7/1971 |

(Continued)

OTHER PUBLICATIONS

Morden et al, Topical Fluoroquinolones for Eye and Ear, 2000, American Family Physician, 62(8), 1870-1876, 8 pages.*

(Continued)

*Primary Examiner* — Trevor Love
(74) *Attorney, Agent, or Firm* — Cooley LLP (57) ABSTRACT

The present invention provides compositions containing (i) a pharmaceutically active agent selected from a group consisting of an arylcycloalkyamine or a derivative, analogue or pharmaceutically active salt thereof, and (ii) a biocompatible polymer or a combination of biocompatible polymers. The compositions or medicaments containing these compositions may be used for the prevention and/or treatment of inner ear diseases, e.g. tinnitus.

9 Claims, 3 Drawing Sheets

In vitro release of ketamine from a hyaluronic acid gel formulation

(56) References Cited

U.S. PATENT DOCUMENTS

| | | | |
|---|---|---|---|
| 5,770,559 | A | 6/1998 | Manning et al. |
| 5,863,927 | A | 1/1999 | Smith et al. |
| 6,017,961 | A | 1/2000 | Flores et al. |
| 6,045,528 | A | 4/2000 | Arenberg et al. |
| 6,066,652 | A | 5/2000 | Zenner et al. |
| 6,120,484 | A | 9/2000 | Silverstein |
| 6,265,379 | B1 | 7/2001 | Donovan |
| 6,309,410 | B1 | 10/2001 | Kuzma et al. |
| 6,316,428 | B1 | 11/2001 | Crandall |
| 6,377,849 | B1 | 4/2002 | Lenarz et al. |
| 6,638,981 | B2 | 10/2003 | Williams et al. |
| 6,656,172 | B1 | 12/2003 | Hildebrand |
| 8,268,866 | B2 | 9/2012 | Guitton et al. |
| 2002/0068718 | A1 | 6/2002 | Pierce |
| 2002/0082554 | A1 | 6/2002 | Lenarz et al. |
| 2002/0161033 | A1 | 10/2002 | Przewosny et al. |
| 2003/0082214 | A1 | 5/2003 | Williams et al. |
| 2003/0143195 | A1 | 7/2003 | Pinsker |
| 2003/0181450 | A1 | 9/2003 | Sundermann et al. |
| 2003/0225116 | A1 | 12/2003 | Chizh et al. |
| 2004/0062819 | A1 | 4/2004 | Hildebrand |
| 2004/0101560 | A1 | 5/2004 | Sawchuk et al. |
| 2005/0267218 | A1 | 12/2005 | Sundermann et al. |
| 2009/0246255 | A1 | 10/2009 | Meyer |

FOREIGN PATENT DOCUMENTS

| | | | |
|---|---|---|---|
| DE | 10124953 A1 | | 12/2002 |
| GB | 1330878 | | 9/1973 |
| JP | 2001-187737 A | | 7/2001 |
| WO | WO 94/08599 A1 | | 4/1994 |
| WO | WO 97/38698 A1 | | 10/1997 |
| WO | WO 98/10757 A2 | | 3/1998 |
| WO | WO 01/10833 A1 | | 2/2001 |
| WO | WO 01/83505 A1 | | 11/2001 |
| WO | WO 01/89505 A1 | | 11/2001 |
| WO | WO 01/98265 A2 | | 12/2001 |
| WO | WO 02/20481 A2 | | 3/2002 |
| WO | WO 03/015699 A2 | | 2/2003 |
| WO | WO 2004/015907 A1 | | 2/2004 |
| WO | WO 2004/022069 A1 | | 3/2004 |
| WO | WO 2004/043902 A1 | | 5/2004 |
| WO | WO2004/050021 | * | 6/2004 |
| WO | WO 2004/050021 A2 | | 6/2004 |
| WO | WO 2004/064912 A1 | | 8/2004 |
| WO | WO 2004/101072 A1 | | 11/2004 |
| WO | WO 2005/073237 A2 | | 8/2005 |
| WO | WO 2005/094799 A2 | | 10/2005 |

OTHER PUBLICATIONS

BASF, Lutrol L and Lutrol F-Grades, Apr. 2010, pp. 1-8.*
Alpini et al., "Tinnitus: pharmacological topodiagnosis," Int. Tinnitus J. 2004; 10(1):91-3.
Azevedo et al., "Transdermal Ketamine as an Adjuvant for Postoperative Analgesia After Abdominal Gynecological Surgery Using Lidocaine Epidural Blockade," 2000, Anethesia & Analgesia, 91, pp. 1479-1492.
Baguley, "Mechanisms of tinnitus," Br. Med. Bull. 2002; 63:195-212. Review. Abstract.
Balough et al., "Kinetics of gentamicin uptake in the inner ear of *Chinchilla langier* after middle-ear administration in a sustained-release vehicle," Otolaryngol. Head Neck Surg. Nov. 1998; 119(5):427-431.
Barnea et al., "Tinnitus with normal hearing sensitivity: extended high-frequency audiometry and auditory-nerve brain-stem-evoked responses," Audiology 1990; 29(1):36-45.
Bans et al., "Intratympanic Steroid Injections for Intractable Meniere's Disease," The Laryngoscope, 111(12):2100-2104 (2001).
Battaglia et al., "Involvement of ras activation in toxic hair cell damage of the mammalian cochlea," Neuroscience 2003; 122(4):1025-35.
Bauer et al., "Assessing tinnitus and prospective tinnitus therapeutics using a psychophysical animal model," J. Assoc. Res. Otolaryngol. Mar. 2001; 2(1):54-64.
Bauer, 2003, "Animal models of tinnitus," Otolaryngol. Clin. N. Am., vol. 36, pp. 267-285.
Bespalov et al., 2000, "Neuropsychopharmacology of NMDA receptor antagonists," S-PB, p. 28.
Bodmer et al., "Rescue of auditory hair cells from aminoglycoside toxicity by *Clostridium difficile* toxin B, an inhibitor of the small GTPases Rho/RadCdc42," Hear Res. Oct. 2002; 172(1-2):81-6.
Boettcher et al., "Salicylate ototoxicity: review and synthesis," Am. J. Otolaryngol. Jan./Feb. 1991; 12(1):33-47.
Borsello et al., "A peptide inhibitor of c-jun N-terminal kinase protects against excitotoxicity and cerebral ischemia," Nat. Med. Sep. 2003; 9(9):1180-6. Epub Aug. 24, 2003.
Cahani et al., "Tinnitus pitch and acoustic trauma," Audiology 1983; 22(4):357-63.
Casado et al., "Opposite modulation of NMDA receptors by lysophospholipids and arachidonic acid: common features with mechanosensitivity," J Physiol. Dec. 1, 1998; 513 (Pt 2):317-30.
Cazals, "Auditory sensori-neural alterations induced by salicylate," Prog. Neurobiol. Dec. 2000; 62(6):583-631.
Chandrasekhar et al., "Dexamethasone pharmacokinetics in the inner ear: Comparison of route of administration and use of facilitating agents," Otolaryngol. Head Neck Surg. Apr. 2000; 122(4):521-528.
Chandrasekhar, "Intratympanic Dexamethasone for Sudden Sensorineural Hearing Loss: Clinical and Laboratory Evaluation," Otology & Neurotology, 22: 18-23 (2001).
Charkevic, 1980, Pharmacology, Medicina, p. 28 (translation attached).
Chen et al., "Pharmacokinetics of Caroverine in the Inner Ear and Its Effects on Cochlear Function after Systemic and Local Administration in Guinea Pigs," Audiol. Neurootol. 8: 49-56 (2003).
Chen et al., "Acute treatment of noise trauma with local caroverine application in the guinea pig," Acta Otolaryngol. Oct. 2003; 123(8):905-9.
Choi et al., "Pharmacology of glutamate neurotoxicity in cortical cell culture: attenuation by NMDA antagonists," J. Neurosci. Jan. 1988; 8(1):185-96.
Chung et al., "Factors affecting the prevalence of tinnitus," Audiology 1984; 23(5):441-52.
Ciocon et al., 1997, "Does oxazepam offer relief of tinnitus or alter it to a non-troublesome functional level in the elderly?" J. American Geriatrics Society, vol. 45 No. 9, Abstract No. P122.
Coad et al., "Characteristics of patients with gaze-evoked tinnitus," Otol. Neurotol. Sep. 2001; 22(5):650-4.
d'Aldin et al., "Implication of NMDA type glutamate receptors in neural regeneration and neoformation of synapses after excitotoxic injury in the guinea pig cochlea," Int. J. Dev. Neurosci. Jul. 1997; 15(4-5):619-29.
Database WPI Week 200169, Abstract of JP 2001-187737, Derwent Publications Ltd, XP002401093 (2001).
Del Bo et al., "Tinnitus aurium in persons with normal hearing: 55 years later," Otolaryngol. Head Neck Surg. Sep. 2008; 139(3):391-4.
Denk et al., "Caroverine in tinnitus treatment. A placebo-controlled blind study," Acta Otolaryngol. Nov. 1997; 117(6):825-30.
Diamond et al., "Systematic review of intratympanic gentamicin in Meniere's disease," J. Otolaryngol. Dec. 2003; 32(6):351-61.
Dobie, "A review of randomized clinical trials in tinnitus," Laryngoscope Aug. 1999; 109(8):1202-11. Review.
Dobie, 2004, "Clincal Trials and Drug Therapy for Tinnitus," in: Tinnitus: Theory and Management; BC Decker, Hamilton-London, pp. 266-277.
Dodson et al., "Intratympanic perfusion for the treatment of tinnitus," Otolaryngol. Clin. North Am. Oct. 2004; 37(5):991-1000.
Dolly et al., "The structure and mode of action of different botulinum toxins," Eur. J. Neurol. Dec. 2006; 13 Suppl. 4:1-9. Review.
Domeisen et al., "Caroverine in tinnitus treatment," Acta Otolaryngol. Jul. 1998; 118(4):606-7.
Dravid et al.,"Subunit-specific mechanisms and proton sensitivity of NMDA receptor channel block," J. Physiol. May 15, 2007; 581(Pt 1):107-28. Epub Feb. 15, 2007.

(56) References Cited

OTHER PUBLICATIONS

Duan et al., "Complementary roles of neurotrophin 3 and a N-methyl-D-aspartate antagonist in the protection of noise and aminoglycoside-induced ototoxicity," Proc. Natl. Acad. Sci. USA Jun. 20, 2000; 97(13):7597-602.

Eggermont et al., "The neuroscience of tinnitus," Trends Neurosci. Nov. 2004; 27(11):676-82.

Ehrenberger et al., "Receptor pharmacological models for inner ear therapies with emphasis on glutamate receptors: a survey," Acta Otolaryngol. Mar. 1995; 115(2):236-40.

Ehrenberger, "Clinical experience with caroverine in inner ear diseases," Adv. Otorhinolaryngol. 2002; 59:156-62.

Ehrenberger, "Topical administration of Caroverine in somatic tinnitus treatment: proof-of-concept study," Int. Tinnitus J. 2005; 11(1):34-7.

Fitzgibbons et al., "Gap detection in normal and hearing-impaired listeners," J. Acoust. Soc. Am. Sep. 1982; 72(3):761-5.

Frank, 2005, "Synthese von dualen NMDA-Rezeptor-/Dopamin-Rezeptor-Liganden," Dissertation, vorgelegt beim FB Biochemie, Chemie and Pharmazie, Johann Wolfgang GoetheUniversitat Frankfurt am Main.

Goycoolea and Lundman, "Round Window Membrane. Structure Function and Permeability: A Review," Microscopy Research and Technique, 36: 201-211 (1997).

Guitton et al., 2004, "Cochlear NMDA Receptors and Tinnitus," Audiological Medicine, vol. 2, No. 1, pp. 3-7.

Guitton et al., "m-Chlorophenylpiperazine exacerbates perception of salicylate-induced tinnitus in rats," Eur. J. Neurosci. Nov. 2005; 22(10):2675-8.

Guitton et al., "New pharmacological strategies to restore hearing and treat tinnitus," Acta Otolaryngol. May 2004; 124(4):411-5.

Hawkins et al., "Interaural time discrimination ability of listeners with sensorineural hearing loss," Audiology 1980; 19(6):495-507.

Hoffer et al., "Sustained-release devices in inner ear medical therapy," Otolaryngologic Clinics of North America, 37: 1053-1060 (2004).

Hoffer et al., "Transtympanic management of tinnitus," Otolaryngologic Clinics of North America, 36: 353-358 (2003).

Horimoto et al., "Developmental changes in arachidonic acid potentiation of NMDA currents in cortical neurones," Neuroreport Nov. 4, 1996; 7(15-17):2463-7.

House et al., "Tinnitus: surgical treatment," Ciba Found Symp. 1981; 85:204-16.

International Pharmaceutical Excipients Council Japan translate edition, "Poloxamer" Handbook of Pharmaceutical Excipients revised edition, Yakuji Nippo Limited, Feb. 28, 2007, pp. 910 through 914.

Jacobson, pp. 194-195, Chapter 7: Physiological Measurement of Tinnitus, in Tinnitus Handbook, Humans, Richard Tyler, Ed. (2000).

Kaltenbach et al., "Plasticity of spontaneous neural activity in the dorsal cochlear nucleus after intense sound exposure," Hear. Res. Sep. 2000; 147(1-2):282-92.

Kemp et al., "NMDA receptor pathways as drug targets," Nat. Neurosci. Nov. 2002; 5 Suppl1:1039-42.

Kenmochi et al., "Salicylate and quinine affect the central nervous system," Hear. Res. Nov. 1997; 113(1-2):110-6.

Koester et al., "Tinnitus—classification, causes, diagnosis, treatment and prognosis," MMW Fortschr Med. Jan. 15, 2004; 146(1-2):23-4, 26-8; quiz 29-30. Review.

Lenarz et al., "Neural mechanisms of tinnitus," Eur. Arch. Otorhinolaryngol. 1993; 249(8):441-6.

Light and Silverstein, "Transtympanic perfusion: indications and limitations," Current Opinion in Otolaryngology & Head and Neck Surgery, 12: 378-383 (2004).

Lobarinas et al., "Salicylate- and quinine-induced tinnitus and effects of memantine," Acta Otolaryngol. Suppl. Dec. 2006; (556):13-9. Abstract.

Lockwood et al., "The functional anatomy of gaze-evoked tinnitus and sustained lateral gaze," Neurology. Feb. 27, 2001; 56(4):472-80.

Maier et al., "Efficacy of the NMDA-receptor antagonist memantine in patients with chronic phantom limb pain—results of a randomized double-blinded, placebo-controlled trial," Pain. Jun. 2003; 103(3):277-83.

Menkes et al., "Sodium valproate for tinnitus," J. Neurol. Neurosurg. Psychiatry Nov. 1998; 65(5):803. Abstract.

Miller et al., "Potentiation of NMDA receptor currents by arachidonic acid," Nature Feb. 20, 1992; 355(6362):722-5.

Nicolas-Puel et al., "Characteristics of tinnitus and etiology of associated hearing loss: a study of 123 patients," Int. Tinnitus J. 2002; 8(1):37-44.

Niedzielski et al., "Expression of AMPA, Kainate, and NMDA receptor subunits in cochlear and vestibular ganglia," J. Neurosci. Mar. 1995; 15(3 Pt 2):2338-53.

Oestreicher et al., "Different action of memantine and caroverine on glutamatergic transmission in the mammalian cochlea," Adv. Otorhinolaryngol. 2002; 59:18-25.

Oestreicher et al., "Memantine suppresses the glutamatergic neurotransmission of mammalian inner hair cells," ORL J. Otorhinolaryngol. Relat. Spec. Jan.-Feb. 1998; 60(1):18-21.

Oestreicher et al., "New Approaches for Inner Ear Therapy with Glutamate Antagonists," Acta Otolaryngol. Mar. 1999; 119(2):174-178.

Olney et al., "Glutamate-induced brain damage in infant primates," J. Neuropathol. Exp. Neurol. Jul. 1972; 31(3):464-88.

Parsons et al., "Memantine is a clinically well tolerated N-methyl-D-aspartate (NMDA) receptor antagonist- a review of preclinical data," Neuropharmacology, 38/6):735-767 (1999).

Pfenninger et al., "Neuroprotektion durch Ketamin auf zellularer Ebene (Neuroprotective effects of ketamine on a cellular level)," Der Anaestesist, 1997.3, vol. 46, Suppl. 1, pp. S47-S54.

Pirvola et al., "Rescue of hearing, auditory hair cells, and neurons by CEP-1347/KT7515, an inhibitor of c-jun N-terminal kinase activation," J. Neurosci. Jan. 1, 2000; 20(1):43-50.

Puel et al., "2002, Treatment of tinnitus. New perspectives," Presse Medical, vol. 31 No. 24, pp. 1137-1143.

Puel et al., "Electrophysiological evidence for the presence of NMDA receptors in the guinea pig cochlea," Hear Res. Feb. 1991; 51(2):255-64.

Puel et al., "Excitatory amino acid antagonists protect cochlear auditory neurons from excitotoxicity," J. Comp. Neurol. Mar. 8, 1994; 341(2):241-56.

Puel et al., "Synaptic regeneration and functional recovery after excitotoxic injury in the guinea pig cochlea," C.R. Acad. Sci. Ill. Jan. 1995; 318(1):67-75.

Puel et al., "Synaptic repair mechanisms responsible for functional recovery in various cochlear pathologies," Acta Otolaryngol. Mar. 1997; 117(2):214-8.

Puel et al., "The inner hair cell synaptic complex: physiology, pharmacology and new therapeutic strategies," Audiol. Neurootol. Jan.-Feb. 2002; 7(1):49-54.

Puel, "Chemical synaptic transmission in the cochlea," Prog. Neurobiol. Dec. 1995; 47(6):449-76.

Pujol et al., "Excitotoxicity, synaptic repair, and functional recovery in the mammalian cochlea: a review of recent findings," Ann. NY Acad. Sci. Nov. 28, 1999; 884:249-54. Review.

Pujol et al., "Implication of non-NMDA and NMDA receptors in cochlear ischemia," Neuroreport. Apr. 1992; 3(4):299-302.

Reyes et al., "Brain imaging of the effects of lidocaine on tinnitus," Hear Res. Sep. 2002; 171(1-2):43-50.

Ruel et al., "AMPA-preferring glutamate receptors in cochlear physiology of adult guinea-pig," J. Physiol. Aug. 1, 1999; 518 (Pt 3):667-80.

Ruel et al., "Salicylate enables cochlear arachidonic-acid-sensitive NMDA receptor responses," J. Neurosci. Jul. 16, 2008; 28(29):7313-23.

Sahley et al., 2001, "A biochemical model of peripheral tinnitus," Hearing Research, vol. 152, pp. 43-54.

Sakata et al., "Treatment of Cochlear-Tinnitus with Dexamethasone Infusion into the Tympanic Cavity," International Tinnitus Journal 2: 129-135 (1996).

(56) References Cited

OTHER PUBLICATIONS

Sala, "Transtympanic administration of aminoglycosides in patients with Meniere's disease," Arch. Otorhinolaryngol. 1988; 245(5):293-6.
Satterfield, "Lidocaine Relieves Tinnitus Sufferers," American Otological Society, press release (2000).
Sattler et al., "Molecular mechanisms of glutamate receptor-mediated excitotoxic neuronal cell death," Mol. Neurobiol. Aug.-Dec. 2001; 24(1-3):107-29.
Scarpidis et al., "Arrest of apoptosis in auditory neurons: implications for sensorineural preservation in cochlear implantation," Otol. Neurotol. May 2003; 24(3):409-17.
Schwab et al., "Use of the round window micro cath for inner ear therapy—results of a placebo-controlled, prospective study on chronic tinnitus," Laryngorhinootologie. Mar. 2004; 83(3):164-72.
Searchfield et al., "Ensemble spontaneous activity in the guinea-pig cochlear nerve," Hear Res. Jun. 2004; 192(1-2):23-35.
Selivanova et al., "The Effects of Streptolysin-O and Sodium Hyaluronate on the Permeability of the Round Window Membrane in Guinea Pigs—an Electrophysiologic Study," Laryngo-Rhino-Otol, 82: 235-239 (2003).
Shulman, "Neuroprotective Drug Therapy: A Medical and Pharmacological Treatment for Tinnitus Control," Int. Tinnitus J. 1997; 3(2):77-93.
Silverstein et al., "Direct round window membrane application of gentamicin in the treatment of Meniere's disease," Otolaryngol Head Neck Surg. May 1999; 120(5):649-55.
Simpson et al., "Recent advances in the pharmacological treatment of tinnitus," Trends Pharmacol. Sci. Jan. 1999; 20(1):12-8.
Sun, pp. 90-91, Tinnitus and Deafness, China Press of Traditional Chinese Medicine (Jan. 2005).
Szczepaniak et al., "Effects of L-baclofen and D-baclofen on the auditory system: a study of click-evoked potentials from the inferior colliculus in the rat," Ann. Otol. Rhinol. Laryngol. May 1995; 104(5):399-404.
Tabuchi et al., "Effect of ketamine, dextromethorphan, and MK-801 on cochlear dysfunction induced by transient ischemia," Ann. Otol. Rhinol. Laryngol. Jan. 2002; 111(1):44-9.
Theopold HM., "Nimodipine (Bay e 9736) a new therapy concept in diseases of the inner ear?" Laryngol. Rhinol Otol. (Stuttg). Dec. 1985; 64(12):609-13.
Timmusk et al., "Identification of brain-derived neurotrophic factor promoter regions mediating tissue-specific, axotomy-, and neuronal activity-induced expression in transgenic mice," J. Cell Biol. Jan. 1995; 128(1-2):185-99.
Togal et al., "Effects of S(+) ketamine added to bupivacaine for spinal anesthesia for prostate surgery in elderly patients," Eur. J. Anaesth. 21:193-197 (2004).
Vane et al., "Mechanism of action of nonsteroidal anti-inflammatory drugs," Am. J. Med. Mar. 30, 1998; 104(3A):2S-8S; discussion 21S-22S.
Vesterarger, "Tinnitus-investigation and management," British Medical Journal, 314 (7082): 728-731 (1997).
Vollenweider et al., "Differential Psychopathology and patterns of cerebral glucose utilisation produced by (S)- and (R)-ketamine in healthy volunteers using positron emission tomography (PET)," Eur. Neuropsychopharmacol. 7:25-38 (1997).
Waddell et al., "Tinnitus," Am. Fam. Physician. Feb. 1, 2004; 69(3):591-2.
Wang et al., "Evaluating effects of some medicine on tinnitus with animal behavioral model in rats", Zhonghua Er Bi Yan Hou Ke Za Zhi. Oct. 2000; 35(5):331-4. Abstract.
Wang et al., "A peptide inhibitor of c-jun N-terminal kinase protects against both aminoglycoside and acoustic trauma-induced auditory hair cell death and hearing loss," J. Neurosci. Sep. 17, 2003; 23(24):8596-607.
Wang et al., "Effects of selective inner hair cell loss on auditory nerve fiber threshold, tuning and spontaneous and driven discharge rate," Hear Res. May 1997; 107(1-2):67-82.
West et al., "Calcium regulation of neuronal gene expression," Proc. Natl. Acad. Sci. USA Sep. 25, 2001; 98(20):11024-31.
Wiechers et al., "A changing pattern of brain-derived neurotrophic factor expression correlates with the rearrangement of fibers during cochlear development of rats and mice," J. Neurosci. Apr. 15, 1999; 19(8):3033-42.
Willingham, 2004, "Tinnitus," Grand Rounds Archieve, Baylor College of Medivine in Houston Texas, Jul. 22, 2004, 8 pages.
Xie, p. 289, Basics and Clinics of Deafness, Hunan Science & Technology Press (May 2004).
Yamakura et al., "Subunit- and site-specific pharmacology of the NMDA receptor channel," Prog. Neurobiol. Oct. 1999; 59(3):279-98.
Ylikoski et al., "Blockade of c-Jun N-terminal kinase pathway attenuates gentamicin-induced cochlear and vestibular hair cell death," Hear Res. Apr. 2002; 166(1-2):33-43.
Zheng, p. 519 and "poloxamer" Handbook of Pharmaceutical Excipients, Chemical Industry Press (Jul. 2004).
Zine et al., "The MAPK/JNK signalling pathway offers potential therapeutic targets for the prevention of acquired deafness," Curr. Drug Targets CNS Neural Disord. Aug. 2004; 3(4):325-32. Review.

\* cited by examiner

Figure 1

In vitro release of ketamine from a hyaluronic acid gel formulation

PHARMACEUTICAL COMPOSITIONS FOR THE TREATMENT OF INNER EAR DISORDERS

CROSS-REFERENCE TO RELATED APPLICATIONS

This application is a continuation of U.S. application Ser. No. 11/992,632, filed on Mar. 26, 2008, which is a national stage application of International Application No. PCT/EP2005/010478, filed on Sep. 28, 2005, the contents of which are hereby incorporated by reference in their entireties for all purposes.

FIELD OF THE INVENTION

The present invention relates to compositions of one or more pharmaceutical compounds for the prevention and/or treatment of tinnitus and other disorders of the inner ear.

BACKGROUND OF THE INVENTION

Various inner ear disorders, e.g. hearing loss, inner ear infectious disease or tinnitus, have attracted increased interest with the object to provide new therapies. E.g. tinnitus, the perception of sound without external acoustic stimulation, is a very common inner ear disorder. An estimated 7% to 14% of the population have talked with their physician about tinnitus, while potentially disabling tinnitus occurs in approximately 1% to 2.4% of people (Vesterarger V., British Medical Journal 314 (7082): 728-731 (1997)). Tinnitus is often associated with other hearing disorders, such as hearing loss or hyperacusis, i.e. hypersensitivity to sound (Sahley T. and Nodar R., Hearing Research (152): 43-54), and quite often originates in the inner ear.

Various pharmaceutical compounds have already been tested in animal models or in human beings for the treatment of inner ear diseases, e.g. tinnitus, such as lidocaine, gabepentin, nortryptline, melatonin, caroverine, baclofen, alprazolam, gacyclidine, 7-chlorokynurenate, or ketamine. While some of them have shown great promise, none of them is in regular clinical use, yet. One of the key obstacles to the development of effective treatments has been the fact that the inner ear is protected like the brain by a biological barrier. For systemic drug administration, relatively high doses are usually required to achieve a desired therapeutic effect in the inner ear, carrying the risk of potent side effects on the central or peripheral nervous system. Topical administration to the inner ear on the other side allows for a targeted delivery of compounds with much lower doses required, as shown by inner ear pharmacokinetic studies (Chen et al., Audiol. Neurootol. 8: 49-56 (2003)). Access to the inner ear may be achieved through a variety of middle-inner ear interface tissue structures, such as the round window membrane, the oval window/stapes footplate, the annual ligament or the endotymphatic sac/endolymphatic duct.

Topical administration of the compound to the inner ear may be accomplished by various delivery techniques. These include the use of devices to transport and/or deliver the compound in a targeted fashion to the membranes of the round or oval window, where it diffuses into the inner ear or is actively infused. Examples are otowicks (see e.g. U.S. Pat. No. 6,120,484 to Silverstein), round window catheters (see e.g. U.S. Pat. Nos. 5,421,818; 5,474,529; 5,476,446; 6,045,528; all to Arenberg, or U.S. Pat. No. 6,377,849 and its division 2002/0082554 to Lenarz), or microimplants (see e.g. WO2004/064912 by Jukarainen et al.). They further include the use of devices which are inserted into the cochlear duct or any other part of the cochlea (see e.g. U.S. Pat. No. 6,309,410 to Kuzma). Another delivery technique is transtympanic injection (sometimes also called "intratympanic injection"), whereas the medication is injected through the tympanic membrane into the middle ear typically for diffusion across the round window membrane (for a description see e.g. Light J. and Silverstein H., Current Opinion in Otolaryngology & Head and Neck Surgery (12): 378-383 (2004). It has been used in clinical practice for a long time and is a relatively minor intervention, which can be carried out in a doctor's office. For repeated injections, a middle ear ventilation tube may be inserted into the tympanic membrane, through which the medication can be administered into the middle ear space. Drug carriers that are too viscous to be injected may also be deposited across a small opening in the tympanic membrane with the aid of surgical instrument.

In order to increase the therapeutic efficacy of pharmaceutical compounds for inner ear therapy, particular formulations with gels, foams or fibrins or other drug carriers can be used. They may provide for the controlled release of the drug over an extended period of time such as hours, days or weeks, improve its diffusion into the inner ear by increasing the permeability of the middle-inner ear interface tissue structure or by keeping the formulation in continuous contact with such structure. This compares favourably to the administration of the pharmaceutical compound in a solution, where multiple injections might be required, drug percolation back into the ear canal or significant loss down the Eustachian tube could result, and continuous contact with the middle-inner ear interface tissue structure might be difficult or impossible to achieve. Ideally, the drug carrier is biocompatible as well as biodegradable, in which case there is no need for subsequent removal.

The diffusion of pharmaceutical compounds across middle-inner ear interface tissue structures, in particular the round window membrane, depends on a variety of factors, such as molecular weight, concentration, liposolubility, electrical charge, and thickness of the membrane (Goycoolea M. and Lundman L., Microscopy Research and Technique 36: 201-211 (1997)). In the absence of experimental data obtained in vivo or with membrane tissue, the capacity to cross middle-inner ear interface tissue structures and thus the suitability of any pharmaceutical compound or formulation for topical administration to the inner ear remains unknown.

Selivanova at al., Laryngo-Rhino-Otol (82): 235-239 (2003) demonstrate in vivo that hyaluronic acid increases the permeability of the round window membrane and that the test substance lidocaine is thus more rapidly diffused into the inner ear and produces a larger effect. Chandrasekhar S., Otology & Neurotology (22): 18-23 (2001) show in vivo that transtympanic injection of dexamethasone with histamine results in higher concentrations of this steroid in the perilymph of the inner ear than if administered without.

There exists vast literature concerning (topical) administration of pharmaceutical compounds to treat inner ear diseases. Steroids and aminoglycosides have been administered locally to the inner ear in clinical practice for quite some time (see e.g. Hoffer et al., Otolaryngologic Clinics of North America (37): 1053-1060 (2004)). Sakata et al., International Tinnitus Journal (2): 129-135 (1996), describe the intratympanic infusion of dexamethasone into the tympanic cavity of human beings. Hoffer et al., Otolaryngologic Clinics of North America (36): 353-358 (2003), describe transtympanic injections of methylprednisolone solutions for the treatment of tinnitus following noise trauma or sudden deafness. In all these cases, the drug compounds were applied in solutions.

However, there is less known about topical treatment of inner ear diseases with other formulations.

WO1997/38698 by Manning et al. teaches the use of biocompatible polymers to deliver pharmaceutical compounds to the inner ear for treating middle and inner ear diseases, e.g. Meniere's disease or viral and bacterial infection diseases. Experimental in vitro release data is shown for a hyaluronic acid formulation with gentamicin.

WO2004/022069 by Puel et al. describes the delivery of neuromodulatory agents, in particular the NMDA antagonists gacyclidine, D-AP5, MK 801 and 7-chlorokynurenate, with a variety of formulations, including drug carriers such as gelfoam, hyaluronic acid, or fibrin glue for the treatment of various inner ear diseases. Moreover, a plurality of alternative insertion methods for administration of the formulation into the middle ear is described by WO2004/022069.

In the light of the literature above and the disadvantages involved with many of the pharmaceutical compositions used so far for topical administration there is a need for other pharmaceutical compositions appropriate for topical treatment of inner ear disorders, which can be easily injected into the middle ear, release the drug over an extended period of time, and allow for a high percentage of the drug to be delivered into the inner ear.

SUMMARY OF THE INVENTION

The present invention provides compositions containing (i) a pharmaceutically active agent selected from a group consisting of an arytcycloalkyamine or a derivative, analogue or pharmaceutically active salt thereof, and (ii) a biocompatible polymer or a combination of biocompatible polymers. These compositions or medicaments containing these compositions may be used for the prevention and/or treatment of inner ear diseases, e.g. tinnitus.

The composition of the present invention comprises a biocompatible polymer support incorporating a therapeutically effective amount of at (east one pharmacologically active agent as defined above. The arylcycloalkylamine agent may e.g. suppress or reduce the perception of tinnitus. Preferably, the composition is formulated such that, upon delivery into the middle ear, it is capable of remaining in contact with at least one of the middle-inner ear interface tissue structures and providing extended release of the pharmacologically active agent into the inner ear. Preferably, the biocompatible polymer is biodegradable as well and may also increase the permeability of the target middle-inner ear interface tissue structure to enhance diffusion of the pharmacologically active agent.

DETAILED DESCRIPTION OF THE INVENTION

The present invention is based on experimental findings with compositions, which are in particular suitable for topical administration of an arylcycloalkylamine, or a derivative, analogue or pharmaceutically active salt thereof, particularly for the treatment of inner ear disorders.

The inventive formulation contains as main pharmacologically active agent a compound of the class of arylcycloalkylamines. Among the class of arylcycloalkylamines compounds having the general formula I wherein R1, R2, R3, R4, R5, R6 and R7 are H, Cl, F, I, $CH_3$, $CH_2CH_3$, $NH_2$, OH, $CONH_2$, COCl or COOH are preferred.

One of the particularly preferred compounds of the class of arylcycloalkylamines is ketamine. Ketamine ($C_{13}H_{16}ClNO$ (free base), 2-(2-chlorophenyl)-2-(methylamino)-cyclohexanone), the structural formula of which is is a non-competitive NMDA-receptor antagonist which binds to the PCP-binding site, a separate site of the NMDA-receptor complex located within the ion channel, thereby blocking the transmembranous ion flux.

Any derivative, analogue, and/or enantiomeric form of ketamine or an arylcycloalkylamine compound as defined by formulae II or I, respectively, may be used as active agent in the inventive composition.

Ketamine may be provided by methods disclosed in U.S. Pat. No. 3,254,124. More specifically, the preferred compound is (S)-Ketamine, as it binds with a 3-4-fold higher affinity to the PCP binding site of the NMDA receptor than (R)-ketamine (Vollenweider et al., *Eur. Neuropsychopharmacol.* 7: 25-38 (1997)). The synthesis of the optical isomers may be carried out as described by DE 2062620 or WO01/98265, which are incorporated herein by reference.

The arylcycloalkylamine compound contained within the pharmaceutical composition of this invention may be provided in the form of a pharmaceutically acceptable salt. Examples of such a salt include, but are not limited to, those formed with organic acids (e.g. acetic, tactic, citric, malic, formaric, tartaric, stearic, ascorbic, succinic, benzoic, methanesulfonic, toluenesulfonic, or pamoic acid), inorganic acids (e.g., hydrochloridic, nitric, diphosphoric, sulphuric, or phosphoric acid), and polymeric acids (e.g., tannic acid, carboxymethyl cellulose, polylactic, polyglycolic, or co-polymers of polylactic-glycolic acids). In a preferred embodiment of the present invention ketamine may be administered as hydrochloride salt ($C_{13}H_{17}Cl_2NO$) of its free base form.

The invention relates to compositions that incorporate an arylcycloalkylamine agent, eventually in combination with at least one other pharmacologically active agent. It may be formulated such that it can be topically administered into the middle ear for controlled release of the agent with the objective of maximizing its passage into the inner ear. Preferably, the composition is adhered to the selected middle-inner ear interface tissue structure by bio-adhesion or mechanical properties.

The biocompatible polymer contained in the inventive composition may support this objectives primarily through two mechanisms. First, by ensuring that the pharmaceutical compound is delivered to the target middle-inner ear interface tissue structure from where it is to diffuse into the inner ear. For this purpose the polymer must remain at the target site for the time that is necessary to achieve the desired duration and effect of the pharmacological treatment either by adhesion to the local middle ear mucosa or through viscous properties, which ensure that the formulation remains in place. Second, by increasing the permeability of the target middle-inner ear interface tissue structure in order to facilitate passage of the pharmaceutical compound into the inner ear.

The composition containing the pharmaceutically active arylcycloalkylamine agent (in the following description often simply designated as "active agent") can have a solid, semisolid, gel-like, or liquid state. Preferably, the composition is a solution, suspension, an emulsion or a thermosetting gel.

The inventive composition contains a biocompatible polymer or a combination of biocompatible polymers. The biocompatible polymer(s) are defined in that they are substantially non-reactive with respect to the human/animal body or bodily fluid. They can be natural, such as naturally occurring polysaccharides, or synthetic in origin.

Preferably, the polymer contained in the composition is degraded in vivo, either hydrolytically or enzymatically, to produce biocompatible, toxicologically safe by-products that are further eliminated by the normal metabolic pathways. A variety of natural, synthetic and biosynthetic polymers are biodegradable. A polymer based on a C—C backbone tends to be nonbiodegradable, whereas heteroatom-containing polymer backbones confer biodegradability. Biodegradability can therefore be engineered into polymers by the appropriate addition of chemical linkages such as anhydride, ester or amide bonds, among others. The degradation is effected by hydrolysis or enzymatic cleavage resulting in a scission of the polymer backbone. Preferred are biodegradable polymers with hydrolysable chemical bonds.

In order to be used in medical compositions the biodegradable polymer must be biocompatible and preferably meet other criteria, such as being biomaterial-processable, sterilizable and capable of controlled stability or degradation in response to biological conditions. Therefore, the degradation products often define the biocompatibility of a polymer, not necessarily the polymer itself.

Poly(esters) based on polylactide (PLA), polyglycolide (PGA), polycaprolactone (PCL) and their copolymers are useful polymers in pharmaceutical compositions. Degradation of these materials yields the corresponding hydroxy acids, making them safe for in vivo use. Other biodegradable polymers include e.g. polyhydroxyalkanoates of the PHB-PHV class, additional polyesters and natural polymers, particularly, modified polysaccharides, e.g. starch, cellulose and chitosan.

The biocompatible polymer can also be selected from block (co)polymers. E.g. multiblock copolymers of poly(ethylene oxide), PEO, and poly(butylene terephthalate), PBT, may be suitable materials. These materials are subject to both hydrolysis (via ester bonds) and oxidation (via ether bonds). Degradation rate is influenced by PEO molecular weight and content. The copolymer with the highest water uptake degrades most rapidly.

The inventive compositions may contain a homogeneous form of a biocompatible polymer or may contain mixtures of one, two or more different polymers, which may be prepared due to a variety of polymers obtained by the production methods resulting in inhomogeneous polymer production or by combining different polymers in a separate mixing step.

The biocompatible polymer used in the present composition preferably can form gels, which may be biodegradable or non-biodegradable, aqueous or non-aqueous, or microsphere based.

Examples of gel forming biocompatible polymers include, but are not limited to, hyaluronic acid resp, hyaluronates, lecithin gels, (poly)alanine derivatives, pluronics, poly(ethyleneglycol), poloxamers, chitosans, xyloglucans, collagens, fibrins, polyesters, poly(lactides), poly(glycolide) or their copolymers PLGA, sucrose acetate isobutyrate, and glycerol monooleate. Preferred are gels which can be easily administered into the middle ear, release the drug over an extended period of time, and allow for a high percentage of the drug to be delivered into the inner ear.

Hyaluronic acid, which is preferably used as biocompatible polymer in the inventive composition, is a physiological substance that is widely distributed in the extracellular matrix of connective tissues in all organs of the body. It occurs in various molecular weights and is reported to be non-antigenic. Moreover, it has an excellent biocompatibility and is also biodegradable. These high molecular weight polymers are widely used in the pharmaceutical and cosmetic industries, e.g. as an ophthalmosurgical aid in various anterior procedures, such as intra- and extra capsular cataract surgery, intraocular lens implantation, keratoplasty, glaucoma surgery and post-trauma surgery. Hyaluronic acids have also found applications in treatment of joint problems. Hyaluronic acid is a naturally occurring polysaccharide, a glycosaminoglycan composed of a long-chain polymer containing repeating disaccharide units of Na-glycuronate-N-acetylglucosamine. The main properties of hyaluronic acid are that it binds water and hence forms a degradable gel with high viscosity. The viscosity of the hyaluronic acid solutions increases with concentration and molecular weight. Pharmaceutically active agents can be either dissolved or suspended in the hyaluronic acid gel.

Phospholipids in conjunction with some other additives have been shown to provide a very promising topical drug delivery vehicle, i.e., lecithin organogel (LO). LOs are thermodynamically stable, clear, viscoelastic, biocompatible, and isotropic gels composed of phospholipids (lecithin), appropriate organic solvent and a polar solvent. The jelly-like phases consist of a three-dimensional network of entangled reverse cylindrical (polymerlike) micelles, which immobilizes the continuous or macroscopic external organic phase, thus turning a liquid into a gel. The formation of a three-dimensional network in the organogel is the result of transition at the micellar level in a low viscous newtonian liquid consisting of lecithin reverse micelles in nonpolar organic liquid. This spherical reverse micellar state of lipid aggregates, turns on to form elongated tubular micelles with the addition of water, and subsequently entangle to form a temporal three-dimensional network in the solution bulk. The latter serves to immobilize the external organic phase, thus producing a gel form or the jelly-like state of the initial nonviscous solution.

Poly(ethyleneglycol), PEG, is a derivative of Poly(ethylene oxide), PEO, which has in addition hydroxyl groups at each end of the molecule. Key properties that make PEG attractive as polymer in pharmaceutical compositions are biocompatibility, hydrophilicity and versality. The simple, water-soluble linear polymer can be modified by chemical interaction to form water-insoluble but water-swellable hydrogels. Absorbent polymers which may function as hydrogels can be prepared e.g. by subjecting the polymers to covalent cross-linking or creating associative polymers consisting of hydrophilic and hydrophobic components ("effective" cross-links through hydrogen bonding).

Thermosetting gels comprise polymers that are fluid at low temperature, but form highly viscous, near solid implants upon placement at a site at body temperature. The most common of these reversible thermosetting systems are poloxamers. When dissolved at concentrations above 20% (w/w), the solutions will remain fluid at low temperatures, but will form highly viscous, solid-like implants upon an increase in temperature (usually around 15° C.). The exact gelation temperature can be altered by changing the poloxamer content or by the addition of other excipients. Once in place, soluble drugs are released by diffusion through the polymer. The polymeric implants do not remain intact for long. At sites where fluid flow is significant (e.g., subcutaneous space), the implants may remain for a period of up to 12-24 hours. The poloxamers are not biodegradable, as they are polyethers (block co-polymers of polyoxyethylene and polyoxypropylene). They are excreted intact in the urine, as they are relatively low molecular weight polymers (<20 kD). They can carry a sizeable drug load, although there is a significant burst effect, especially for hydrophilic drugs. The kinetic profile for hydrophobic drugs tends to be retarded, presumably by sequestration of the drug within a hydrophobic core of the implant.

Thermosetting gels that are biodegradable and have slower release characteristics than poloxamers include PLA-PEG or triblock copolymers of PEG-PLGA-PEG. As with the poloxamer systems, they are fluid at low temperature. Upon administration they form a semi-solid gel.

Chitin is the second most abundant natural polymer in the world after cellulose. Upon deacetylation, it yields the biomaterial Chitosan, which upon further hydrolysis yields an extremely low molecular weight oligosaccharide. Chitosan has biocompatible and antibacterial properties. A chitosan-glycerolphosphate solution is able to form a reversible thermosetting gel. Again, it is fluid at low temperatures and forms a semi-solid upon administration at body temperature. For example, this system can be used to deliver growth hormone. Chitosan remains soluble in water up to pH 6.2. Any pH above this value leads to charge neutralization and precipitation of the polymer. Addition of sugar-based phosphates transforms chitosan into a thermo-reversible gel drug delivery system.

Besides the thermally reversible gels other stimuli-responsive polymers which are critically reliant on the balance between polymer-polymer and polymer-solvent interactions under various stimuli including changes in temperature, pH, ionic strength, solvent concentration, pressure, sheer stress, light intensity, electric or magnetic fields or a combination of these factors may be suitable in the present composition. An example of a pH-reversible hydrogel is the aqueous solution of poly(acrylic acid) polymer, which undergoes a pH-mediated phase transition at concentrations above 0.1% by weight.

The stimulus-sensitive gel may be also formed from an enzymatically degradable polypeptide polymer. The polypeptide bonds in the polypeptide polymer are more stable against hydrolysis than e.g. the ester bonds in PEG/PLGA polymer systems, thereby also providing superior storage stability. The polypeptide carrier may also include a biodegradable polymer having a biodegradable polypeptide block linked to a second polymer block to form a graft or linear polymer. An example for a polypeptide polymer is poly(alanine) and derivatives thereof. The polypeptide carrier may also be a protein matrix known as fibrin. Fibrinogen is a naturally occurring protein which, when combined with the enzyme thrombin, another naturally occurring protein, forms a bio-matrix known as fibrin Other biocompatible polymers may also be used including starch, celluloses, gelatins pluronics, tetronics, the latter two being poly(ethylene oxide)/poly(propylene oxide) materials. Other materials that may be used include the chondroitin sulfates and the general class of mucopolysaccharides (e.g., glycosaminoglycans) and other biocompatible polymers having characteristics similar to hyaluronic acid.

A medicament containing the inventive composition is preferably formed as a release-of-drug-formulation which releases the pharmaceutically active agent(s) over several hours up to several weeks.

In a first embodiment of the present invention, the active agent(s) form(s) a core surrounded by an inert diffusion barrier formed by the biocompatible polymer. These systems include e.g. membranes, capsules, microcapsules, liposomes and hollow fibers. Here, the release of the active agent is mainly controlled by diffusion.

In a second embodiment, the composition comprises a solution of the biocompatible polymer wherein the active agent is dissolved, emulsified or dispersed. As in reservoir systems, the diffusion of the active agent(s) through the polymer matrix is the rate-limiting step, and release rates are determined by the choice of polymer and its consequent effect on the diffusion and partition coefficient of the active agent to be released.

In another embodiment of the present invention, the composition comprises a cross-linked polymer gel forming a macromolecular "cage" in which the active agent is dispersed. Alternatively, the present composition may comprise a cross-linked mixed gel consisting of a combination of biocompatible hydrophilic polymers in which the active substance is dispersed.

In a further embodiment, the composition comprises a cross-linked gel of the biocompatible polymer or cross-linked mixed gel of at least two hydrophilic polymers containing the active agent which is covalently attached to the macromolecules of at least one of the polymers.

The release rate of pharmaceutical compounds from polymer based gels may be extended by such cross-linking, whereas adjacent chains of the polymer are joined by creating covalent bonds. The resulting cross-linked polymer breaks down more slowly and thus retains the pharmacologically active agent longer.

Various cross linking agents and methods for accomplishing cross linking of biodegradable materials are well known in the art. Preferably, cross linking is accomplished so that the final cross linked material for the delivery unit are substantially non-toxic (e.g., by use of thermal cross linking, gamma irradiation, ultraviolet irradiation, chemical cross linking, etc.). In general, the degree of cross linking relates inversely to the degree of swelling or absorption of water by the shaped polymer structure. The degree of swelling or water absorption regulates the rate of drug transport by the polymer structure.

In a further embodiment of the present invention the release of the active agent from the polymer is chemically controlled. This control can be achieved using bioerodible or pendant chains. Polymer bioerosion can be defined as the conversion of a material that is insoluble in water into one that is water-soluble. In such a system the active agent is ideally distributed uniformly throughout the polymer. As the polymer surrounding the active agent is eroded, the active agent escapes. In a pendant chain system, the active agent is covalently bond to the polymer and is released by bond scission owing to water or enzymes. In solvent-activated controlled systems, the active agent is dissolved or dispersed within a polymer matrix and is not able to diffuse through the matrix. In one type of solvent controlled systems, as the environmental fluid, e.g. water, penetrates the matrix, the polymer swells and its glass transition temperature is lowered below the environmental temperature. Thus, the swollen polymer is in a rubbery state and allows the drug contained within to diffuse through the encapsulant.

Another technique to extend the release rate of ionic compounds is by incorporating the pharmacologically active agent in a hydrophobic ion pair complex as described in WO1997/38698. Here, the pharmacologically active agent may be present in the form of a hydrophobic ion pair complex with an amphiphilic material. Preferred amphiphilic materials for forming a hydrophobic ion pair with the arylcycloalkylamine active agent are sodium dodecyl sulfate (SDS) and bis-(2-ethylhexyl) sodium sulfosuccinate (AOT). The hydrophobic ion pair complex may be prepared according to procedures known in the art. Additional information concerning hydrophobic ion pair complexes and their preparation may be found in PCT Publication No. WO 94/08599, published Apr. 28, 1994, and pending U.S. patent application Ser. No. 08/473,008, filed Jun. 6, 1995, the contents of both of which are incorporated herein in their entireties.

It is also possible to combine the embodiments described above allowing the controlled release of the active agent, for example by creating a gel holding microspheres. There, the release of the active agent may be controlled by the gel system as well as by the microspheres suspended in the polymer gel system.

Most any of the viscous gel systems described above (e.g. hyaluronate) could be designed to hold suspended microspheres. The gel could provide an intimate contact to the middle inner ear interface tissue structure and thus allow the transport of the active agent(s) through the membrane into the inner ear by the microspheres. Active agent release rates depend very strongly on the size of the microspheres containing the active agent, larger microspheres may generally release encapsulated compounds more slowly and over longer time periods. To achieve a delivery of the active agent at a constant rate it might be useful to mix microspheres of different sizes to generate a constant rate of release over a prolonged period of time. Moreover, the gel containing the microspheres may also contain substances increasing the permeability of the membrane so that the microspheres can pass the membrane more easily.

The different systems described above suitable for the controlled release of the active agent may also be included in an implant which could be placed e.g. at the round window membrane and delivers the active agent in a controlled manner.

In one embodiment, the implant consists essentially of a carrier medium which is combined with the active agent. The carrier medium may comprise the biocompatible polymer which may be biodegradable or not, or a combination of biocompatible polymers which may be cross-linked. This composition may be formed such that it is injectable and modifies its viscosity, e.g. from fluid to highly viscous or solid, upon insertion into the middle ear, as described above for the thermosetting gels, e.g. poloxamers. Release of the active agent contained in the carrier medium may be by diffusion, solvent drag, electrodiffusion, osmosis, active/passive transport or a combination thereof.

In another embodiment, the implant may comprise a core and at least one membrane encasing the core. The core may comprise the composition consisting of the active agent(s) dissolved or dispersed in the biocompatible polymer(s). The membrane can be made of the same or a different polymer composition than the core or an elastomer composition. In this implant the release rate of the active agent is controlled by the properties of the core and optionally by the properties of the membrane(s). Thus, the release rate(s) of the active agents can be controlled either by the core or membrane alone or by the membrane together with the core. It is also possible, that the release rate is mainly controlled by the core and that the membrane performs only the final control of the release rate.

If the membrane encasing the core consists of two or more layers, the polymer or elastomer compositions used in each layer may be same or different. The combination of different layers of membrane either in thickness or in material or both gives a further possibility for controlling the release rate of the active agent(s).

If the implant comprises more than one pharmaceutically active agent, the core may consist of one part comprising the different active agents dissolved or dispersed in the same polymer composition. In another embodiment, the core consists of at least two parts, each part comprising at least one pharmaceutically active agent. The polymer compositions of the different parts of the core may be chosen according to the desired release rates of the different active agents and may therefore same or different in each part. The different parts of the core may be either positioned next to each other or in such a way that one part of the core encases at least partly another part of the core. The different parts of the core may be either spaced from each other and/or may be separated by a separating membrane. The separation membranes may be permeable or impermeable to at least one of the pharmaceutically active agents. Also it is possible to use a membrane which is permeable to a first active agent but impermeable to a second active agent.

Useful as materials of the membrane(s) of the implant are e.g. siloxan-based elastomers which are elastomers made of poly(disubstituted siloxanes) where the substituents mainly are lower substituted or unsubstituted alkyl or phenyl groups. A widely used and preferred polymer of this kind is poly (dimethylsiloxane). Also ethylene-vinylacetate copolymer membranes which can act as rate-limiting barrier for the diffusion of the active agent may be suitable.

The release kinetics of the pharmacologically active agent are not only governed by the release from the composition, but to a potentially even more important extent by the degree of permeation of the inner-middle ear interface tissue structure.

Therefore, pharmaceutical compositions of this invention suited for topical administration to the inner ear preferably contain substances increasing the permeability of the middle-inner ear interface tissue structure in a way that the pharmacologically active agent can diffuse in a given period of time in higher quantities or in a given quantity more quickly into the inner ear or that a larger molecule could pass into the inner ear. Such improved permeation must come however without disturbing the osmotic balance between inner ear perilymph and the middle ear space and without inducing toxicity in the cochlea. Particular attention has to be paid to potential ototoxicity from permeability enhancing substances, which may themselves pass across the round window and have a cytotoxic effect within the inner ear. It could e.g. be shown that streptolysin does well increase round window permeability, yet at the price of cytotoxicity.

An example for a substance increasing the permeability of the middle-inner ear interface tissue structure is histamine. Also, hyaluronic acid has been shown to increase the permeability of the inner-ear interface structure without ototoxicity and is therefore preferably used as biocompatible polymer in the composition of the present invention.

The composition of the present invention may further comprise one or more other pharmacologically active compounds. Otic compositions in accordance with the present invention can comprise various ingredients, including other biologically-active-agents, such as antibiotics, e.g., fluoroquinolones, anti-inflammatory agents, e.g., steroids, cortisone, analgesics, antipyrine, benzocaine, procaine, antioxidants, e.g. methionine, N-acetylcysteine, trolox, neurotrophins, e.g. GDNF or BDNF, anti-apoptotic or anti-necrotic agents, e.g. leupeptin, caspase inhibitors, etc.

Pharmaceutical compositions of this invention suited for topical administration to the inner ear contain a therapeutically effective amount of active ingredient(s), and, as may be necessary, further components such as inorganic or organic, solid or liquid pharmaceutically acceptable carriers or vehicles, buffers, excipients and additives.

Suitable vehicles for topical administration are organic or inorganic substances, which are pharmaceutically acceptable and which do not react with the active compounds, for example saline, alcohols, vegetable oils, benzyl alcohols, alkylene glycols, polyethylene glycols, glycerol triacetate, gelatin, carbohydrates such as lactose or starch, magnesium, stearate, talc and petrolatum. The indicated preparations can be sterilized and/or contain ancillary substances such as lubricants, preservatives, such as thiomersal (e.g., at 50%), stabilizers and/or wetting agents, emulsifiers, salts to influence the osmotic pressure, buffer substances, colorants, and/or aromatizing substances.

Preferably, a topical excipient is selected that does not enhance delivery of the agent to the systemic circulation or to the central nervous system when administered to the ear. For example, in general, it is preferred that the topical excipient has not substantial occlusive properties, which enhance percutaneous transmission through the mucosa into the systemic circulation. Such occlusive vehicles include hydrocarbon bases, anhydrous absorption bases such as hydrophilic petrolatum and anhydrous lanolin (e.g., Aquaphor), and water-in-oil emulsion bases such as lanolin and cold cream. More preferred are vehicles which are substantially non-occlusive, and generally include those which are water-soluble, such as oil-in-water emulsion bases (creams or hydrophilic ointments) and water-soluble bases such as polyethylene glycol-based vehicles and aqueous solutions gelled with various agents such as methylcellulose, hydroxyethyl cellulose, and hydroxypropylmethylcellulose (e.g., K Y Gel).

Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87. For instance, biologically-active agents in accordance with the present invention can be combined with enhancing agents which enhance the penetration of an agent.

The pharmaceutical composition containing the active ingredient(s), the biocompatible polymer(s) and, if necessary, adjuvants, e.g. preservatives, stabilizers, wetting agents, emulsifiers, cross-linking agents, may be prepared by any of the methods well known in the art of pharmacy, e.g. by conventional mixing, granulating, confectioning, dissolving or lyophilizing methods.

The composition can be used for the preparation of a medicament for treating inner ear diseases. Examples are the treatment of tinnitus, hearing loss, inner ear inflammation or infection, autoimmune ear disorder, vertigo, Meniere's Disease, inner ear cell degeneration or age-induced inner ear cell degeneration.

Administration of the inventive composition or medicament to a mammal suffering from an inner ear disease may be accomplished by various delivery techniques. Preferably, it is administered by inserting it into the middle ear. The medicament resp. implant preferably can be administered by infusion, injection or by deposition by means of a surgical instrument.

These include the use of devices or drug carriers to transport and/or deliver the formulation in a targeted fashion to the inner-middle ear interface tissue structures, where it diffuses into the inner ear or is actively infused. Examples are otowicks (see e.g. U.S. Pat. No. 6,120,484 to Silverstein), round window catheters (see e.g. U.S. Pat. Nos. 5,421,818; 5,474,529; 5,476,446; 6,045,528; all to Arenberg, or U.S. Pat. No. 6,377,849 and its division 2002/0082554 to Lenarz), micro-implants (see e.g. WO2004/064912 by Jukarainen et al.) or devices which are inserted into the cochlear duct or any other part of the cochlea (see e.g. U.S. Pat. No. 6,309,410 to Kuzma). They further include the use of intratympanic injection, where the formulation is injected into the middle ear over the area of the target inner-middle ear interface tissue structure, such as the round window niche (see e.g. Light J. and Silverstein H., *Current Opinion in Otolaryngology & Head and Neck Surgery* 12: 378-383 (2004)). The injection may be performed directly through the tympanic membrane, through a ventilating tube inserted into the tympanic membrane, or through an opening of the tympanic membrane (e.g. by tympanomeatal flap). The volume of the formulation to be injected is typically between 200 and 500 microliters.

Formulations which cannot be injected or infused by any of the aforementioned means may be deposited onto the target inner-middle ear interface structure across a small opening in the tympanic membrane with the aid of surgical instrument.

The formulation can be administered prior to, during or after the onset of the inner ear disorder. The amount to be administered may vary, depending upon the method of administration, duration of therapy, the condition of the subject to be treated, the severity of the inner ear disorder and ultimately will be decided by the attending physician. The duration of therapy may range between about one hour and several days, weeks or months, and may extend up to chronic treatment. In the case of therapies of long duration, repeat doses of the formulation may have to be administered. The therapeutically effective amount of the compound to be delivered may range between about 0.1 nanogram/hour to about 100 micrograms/hour.

A therapeutically effective dose is defined as an amount effective to suppress or reduce the inner ear disorder in a treated individual. A therapeutically effective dose is also the amount effective to suppress or reduce the inner ear disorder in the afflicted individual. As stated above, a therapeutically effective dose may vary, depending on the choice of specific compound, the specific condition to be treated and on the method of its administration. For example, a lower dose of a ketamine analogue with a higher binding affinity may be more effective than ketamine that binds with a lower affinity. As a result, arylcycloalkylamines with higher binding affinities are preferred.

The duration of therapy may also vary, depending on the specific form of inner ear disorder for which treatment is desired—acute, subacute, or chronic. As a guide, shorter durations of therapy are preferred and are sufficient when the inner ear disorder does not recur once therapy has ceased. Longer durations of therapy may be employed for an individual in which the inner ear disorder persists following short therapy.

The present invention is explained in more detail by the following Examples in conjunction with the attached Figures without limiting the scope of the present invention.

Figure 1:
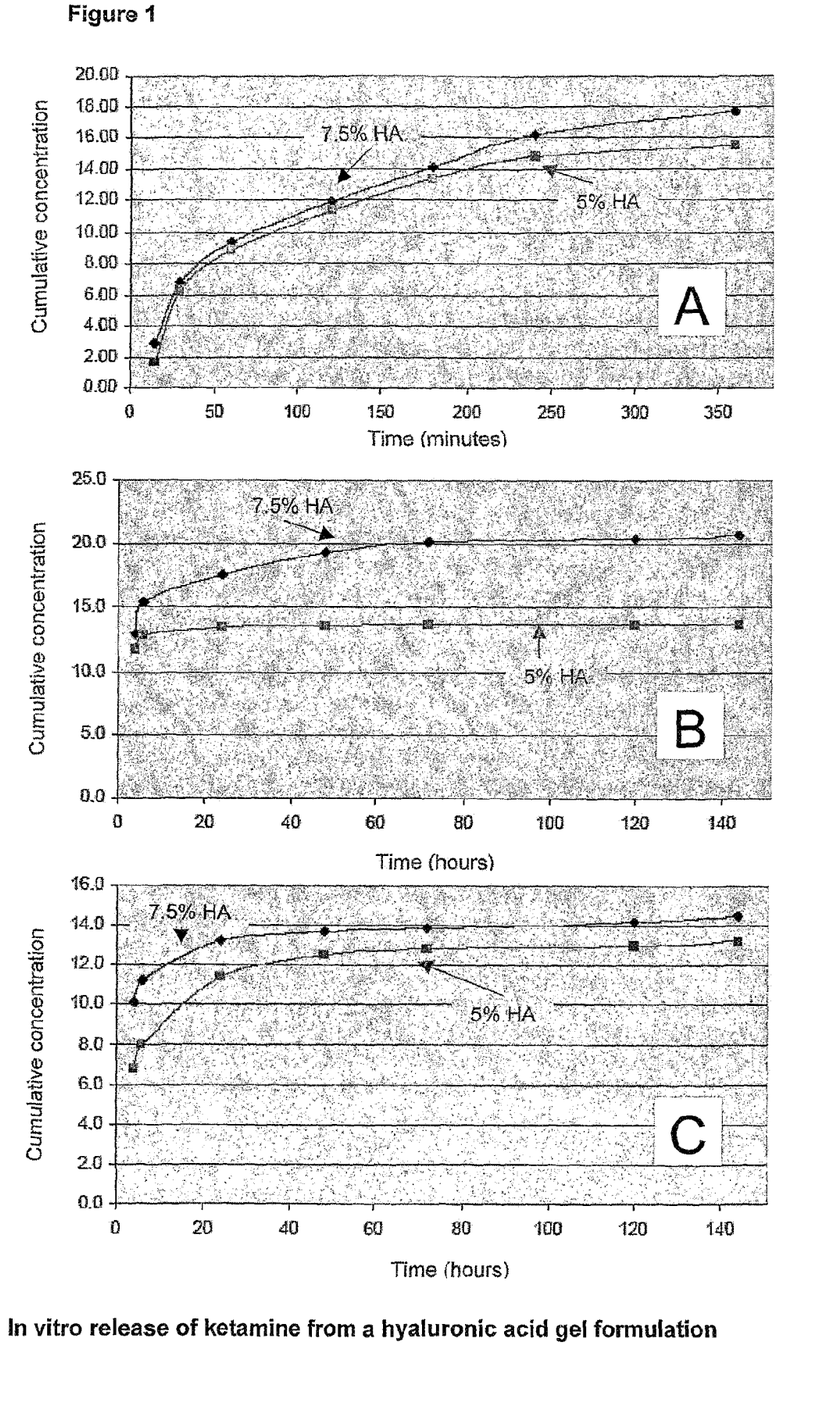
FIG. 1 shows the cumulative release of S-(+)-Ketamine from 5% and 7.5% hyaluronic acid gel formulations into phosphate buffer solution over time.

FIG. 1 shows the cumulative release of S-(+)-Ketamine from 6% and 7.5% hyaluronic acid gel formulations into phosphate buffer solution over time. (A) Ketamine is rapidly released from the gel in the absence of a rate limiting membrane; after just one hour almost 50% of the total cumulative concentration in PBS are already achieved. The concentration of hyaluronic acid has hardly any effect on the release rate. (B) The use of a Franz cell with a dialysis membrane to mimic the round window membrane slows down significantly the release of Ketamine into PBS, which now takes about three days. The release rate appears to be much slower for the higher concentration of hyaluronic acid. (C) When a filter membrane is employed in the Franz cell, the release of Ketamine extends over approximately 60 hours, with the more highly concentrated hyaluronic acid gel releasing more slowly than at the lower concentration.

Figure 2:
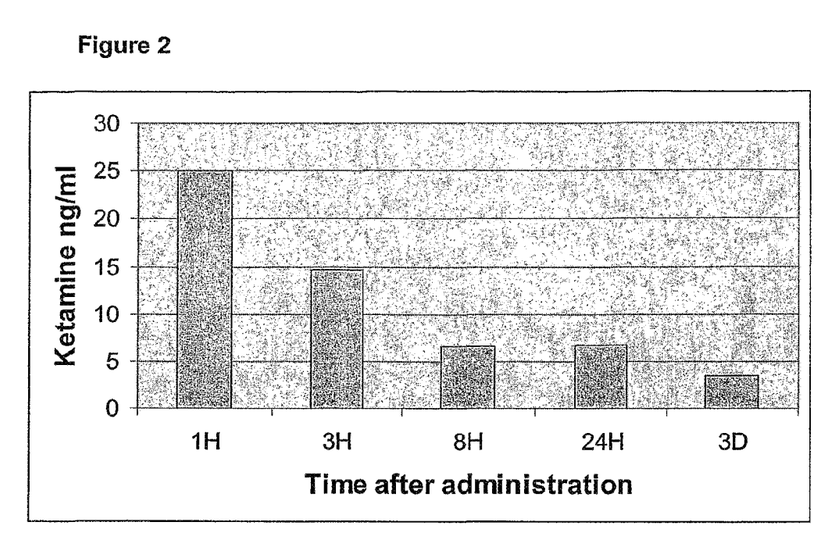
FIG. 2 shows release of ketamine in a hyaluronic acid formulation across the round window membrane into cochlear perilymph. The figure shows that the concentration of S-(+)-Ketamine in perilymph after being released from a 2.8% hyaluronic acid formulation that had been placed into the round window niche of guinea pigs and then diffused across the round window into the inner ear.

FIG. 2 shows the concentration of S-(+)-Ketamine in perilymph after being released from a 2.8% hyaluronic acid formulation that had been placed into the round window niche of guinea pigs and then diffused across the round window membrane into the inner ear. Perilymph was sampled to determine Ketamine concentration at the time points 1 hour (1 H), 3 hours (3 H), 8 hours (8 H), 24 hours (24 H) and 3 days (3 D).

Figure 3:
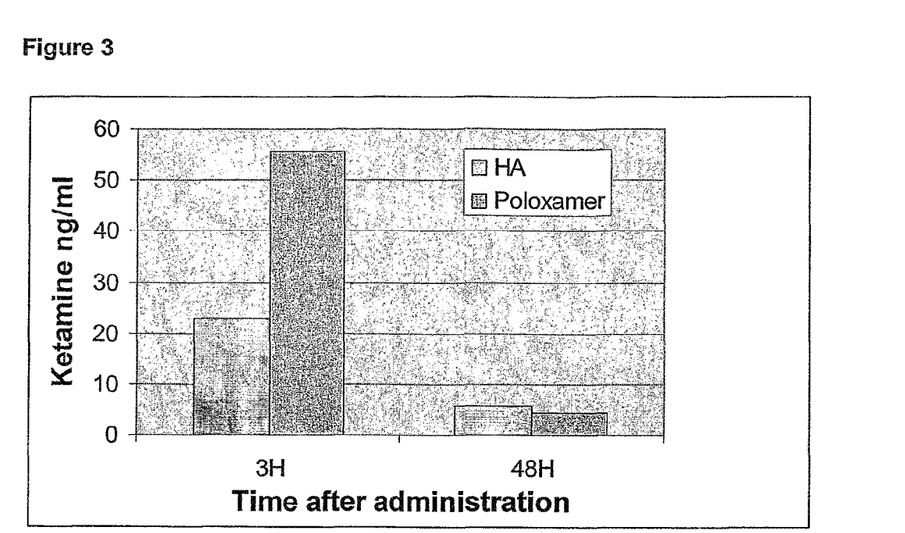
FIG. 3 shows release of ketamine in formulations with hyaluronic acid or poloxamer across the round window membrane into cochlear perilymph. The figure shows that the concentration of S-(+)-Ketamine in perilymph after being released either from a 0.7% hyaluronic acid formulation or a 20% poloxamer formulation that had been injected into the round window niche of guinea pigs and then diffused across the round window into the inner ear.

FIG. 3 shows the concentration of S-(+)-Ketamine in perilymph after being released either from a 0.5% hyaluronic acid formulation or a 20% poloxamer formulation that had been injected onto the round window niche of guinea pigs and then diffused across the round window membrane into the inner ear. Perilymph was sampled 3 hours and 48 hours post administration to determine Ketamine concentrations.

Example 1

Methods and Materials

The release of the NMDA receptor antagonist Ketamine, which had been previously shown to be effective in the treatment of cochlear tinnitus, from a hyaluronic acid gel formulation was evaluated in a two staged approach. In a first stage, in vitro experiments were performed to determine the release kinetics of the formulation. These results were then used as starting point for in vivo studies in animals.

In Vitro Studies

A hyaluronic acid solution (Hylumed, Genzyme Corp.) was prepared at concentrations of 5 and 7.5% in phosphate buffered saline (PBS). At 8%, handling of the gel had shown to be difficult due to the high viscosity. S-(+)-Ketamine hydrochloride (Sigma-Aldrich) was dissolved at a concentration of 2% (weight/weight) equivalent to 73 mM. To evaluate the importance of the drug load factor, concentrations of 0.5% and 2.5% were also tested. Release of the pharmacologically active agent was measured in PBS, a common receiver fluid for controlled release studies, either without any membrane or by using a filter membrane or a dialysis membrane (Spectropore) in a Franz cell (PermeGear). The membranes were employed to mimic the rate limiting membrane of the round window. The temperature of the fluid was maintained constant at body temperature. The bottom chamber of the Franz cell was filled with 5 ml of PBS as the receiver fluid. The receiver fluid contained a stir bar for continuous agitation. The upper chamber was filled with approximately 50 mg of gel and the cell assembled. At various time points, aliquots (typically 1 ml) were withdrawn and analyzed by UV spectrophotometry (Agilent 8453). The absorbance at 215 nm was measured and the concentration calculated using an extinction coefficient of 30 ml/mg cm. As the volume of the aliquot was known, the total amount released could be determined. Each time an aliquot was withdrawn, the same volume of PBS was placed back into the Franz cell chamber.

In Vivo Studies

Based on the results of the in vitro studies, various concentrations of hyaluronic acid (Hylumed Medical, molecular weight 2.4 million, Genzyme Corp.) were tested for their residency in the round window niche and their potential effect on hearing through interference with the free movement of the round window membrane. Hearing thresholds were tested in pigmented guinea pigs by measuring the compound action potential (CAP) of the auditory nerve by an electrode implanted onto the round window membrane of the animals (with a reference electrode placed in a neck muscle). The reference electrode and the round window electrode were soldered to a plug fixed on the skull. For this purpose and administration of 2 microliters of the gel formulation into the round window niche, the bulla of the anaesthetized animal was opened through a posterior auricular surgical procedure (dorsal approach). The bulla was then closed again with dental cement (Texton, SS White Manufacturing), the wounds disinfected with a betadine solution and sutured.

First, a gel was prepared at the concentration of 5% in artificial perilymph, which had previously been tested in the in vitro tests, and deposited with the tip of a previously sterilized surgical instrument into the round window niche of a guinea pig. The residency of the gel within the niche was visually inspected, i.e. whether the gel flowed out of it or remained in place. The CAP was measured just prior to the gel administration and then again repeatedly after the administration. As the viscosity of the gel was too high, and transitory effects on hearing threshold levels were observed, the gel concentration was then titrated down (3.5%, 3.2%) to finally 2.8%, a level at which the gel could conveniently be placed into the round window niche, remained well in place and no hearing loss was observed. One animal per concentration was tested.

In a second step, a pharmacokinetic study with pigmented guinea pigs was carried out in order to evaluate in vivo the diffusion of Ketamine from a hyaluronic acid gel formulation across the round window membrane into the inner ear. A total of 30 animals were tested for concentrations of the pharmaceutical compound in the perilymph at 1 hour, 3 hours, 8 hours, 24 hours and 72 hours following gel administration; 6 animals per time point were tested.

Animals were anaesthetized with a single-dose i.p. injection of 0.3 ml/kg of pentobarbital at 6% (Ceva sante animale), and the right ear bulla was opened using a posterior auricular surgical procedure (dorsal approach). 2 microliters of the hyaluronic gel formulation (2.8% Hylumed Sterile in artificial perilymph, molecular weight 2.44 million; Genzyme Corp.) with S-(+)-Ketamine (Sigma-Aldrich) at a concentration of 1 milliM were then deposited onto the round window membrane of the inner ear. At each of the aforementioned time points, one group of animals was decapitated under deep anaesthesia (pentobarbital 50 mg/kg). The right cochlea was extracted from the temporal bone and the bulla opened. A small hole was then drilled into the cochlea by cochleostomy (diameter 0.2 mm) at its base. 10 microliters of perilymph were sampled through the hole with a sterile glass micropipette (0.1 mm diameter at the tip), connected by a sterile catheter to a sterile microsyringe. The samples were then analyzed by liquid chromatography mass spectrometry with a limit of quantification of 0.2 ng/ml (HPLC instrument: Perkin Elmer series 200; mass spectrometer detector: MSD Sciex API 4000 Applied Biosystems; column: Zorbax SB CN 50×2.1 mm 5 µm-Agilent technologies).

Results

In Vitro Studies

As FIG. 1 shows, the hyaluronic acid gel releases Ketamine relatively quickly, i.e. over just a few hours. The release kinetics are significantly altered when a rate limiting membrane is employed, with the delivery now extending over a few days. At the higher concentration of 7.5%, the hyaluronic acid get formulation releases Ketamine less quickly than at 5%.

The drug load had also a significant influence on release kinetics. When the gel contained 0.5% Ketamine (by weight), the pharmaceutical compound was released in a Franz cell with filter membrane nearly as fast as a simple Ketamine hydrochloride solution. Only by increasing the loading factor to 2.5% did the release kinetics slow appreciably. The initial burst was quite low, with only about 20% being released in the first hour. Therefore, it appears that using as high a loading factor as possible will help extend the release kinetics.

In Vivo Studies

As FIG. 2 shows, the maximum concentration of Ketamine in the perilymph of the inner ear following diffusion across the round window membrane from a 2.8% hyaluronic acid gel is achieved within one hour. Concentrations then decrease rapidly, with the last quantifiable levels observed after three days. Several interesting conclusions can be drawn from these results:
1) The gel formulation has the capacity to release Ketamine into the inner ear over three days—in spite of a much lower concentration of hyaluronic acid (2.8% vs. 5 resp. 7.5%) and a drug load that is about 73 fold lower (0.027% vs. up to 2.5% by weight) than in the in vitro experiments. It thus seems to be an attractive type of formulation for the treatment of inner ear disorders.
2) The measured perilymph concentrations of Ketamine appear very low when compared with the initial concentration of the pharmacologically active agent in the gel. This may be explained by loss of the Ketamine into the middle ear, absorption by the mucosa, the incapacity of the passive diffusion process to pull more of the pharmaceutical compound into the perilymph, or a rapid clearance of the drug from the perilymph. In addition, the sampling technique leads to a downward bias in measured concentrations, as minimum quantities require that perilymph is pulled also from parts within the inner ear to which the pharmaceutical compound has probably not been distributed. I.e. there is a dilution of concentrations. It is well known in the Art that concentrations of pharmaceutical compounds within the cochlea are highest at its base, much lower in the middle turn and mostly absent in the apical region and beyond (scala vestibuli).
3) Given the many parameters which can influence the release kinetics from a gel formulation placed into the round window niche and the diffusion across the round window niche, in vitro models must be considered as very limited in their ability to evaluate whether and how a pharmacologically active agent for the treatment of an inner ear disorder is delivered into the inner ear. The use of an appropriate in vivo model seems thus to be imperative.

Example 2

While the previous experiments explored release kinetics of Ketamine from a rather viscous gel formulation, which could not be injected into the middle ear, we sought next to evaluate two injectable gel formulations, which offer the advantage of easy handling.

Methods and Materials

A total of 16 pigmented guinea pigs were administered 100 microliters of either a hyaluronic acid (Hylumed Sterile, Genzyme Corp.) or a poloxamer (Lutrol F127, BASF) gel formulation containing S-(+)-Ketamine hydrochloride (Cristalia) through a 1 ml syringe connected to a needle. Half of the animals received 0.5% hyaluronic acid gel prepared in a phosphate buffered solution at pH 7.4 prepared in accordance with the European Pharmacopoeia (ref. 4005000). The Ketamine was dissolved in the gel at a concentration of 1 mM with a magnetic stirrer over night at 4 degrees Celcius. The remaining half of the animals received a 20% poloxamer gel also through a 1 ml syringe connected to a needle. The gel was prepared by adding slowly 600 mg of Lutrol powder to 3 ml of the same phosphate buffered solution in a magnetic stirrer (500 rpm). The mixing process continued then for 16 hours to obtain a clear solution with minimum viscosity. As for the hyaluronic acid gel, the Ketamine was dissolved in the poloxamer solution at a concentration of 1 mM with a magnetic stirrer over night. Immediately after contact with the middle ear tissue of the guinea pigs, the poloxamer gelified and became almost solid.

In order to inject the gel formulations, the guinea pigs were anaesthetized with a single-dose i.p. injection of 0.3 ml/kg of pentobarbital at 6% (Ceva santé animale) and the right bulla of the animal was opened through a posterior auricular surgical procedure (dorsal approach). The bulla was then closed again with dental cement (Texton, SS White Manufacturing), the wounds disinfected with a betadine solution and sutured. After 3 hours, 4 animals of each gel formulation group were decapitated under deep anaesthesia (pentobarbital 50 mg/kg) to sample the perilymph, with the remaining animals being sacrificed after 48 hours. The right cochlea was extracted from the temporal bone and the bulla opened. A small hole was then drilled into the cochlea by cochleostomy (diameter 0.2 mm) at its base. 10 microliters of perilymph were sampled through the hole with a sterile glass micropipette (0.1 mm diameter at the tip), connected by a sterile catheter to a sterile microsyringe. The samples were then analyzed by liquid chromatography mass spectrometry with a limit of quantification of 0.2 ng/ml (HPLC instrument: Perkin Elmer series 200; mass spectrometer detector: MSD Sciex API 4000 Applied Biosystems; column: Zorbax SB CN 50×2.1 mm 5 µm-Agilent technologies).

Results

As FIG. 3 shows, the use of a less viscous hyaluronic acid formulation did not change significantly the concentration in the perilymph at the time points of 3 hours and 48 hours after administration. This shows that an injectable formulation provides for a similar concentration in the inner ear. FIG. 3 further shows that poloxamers also provide for effective release across the round window membrane, whereas the concentration in perilymph at three hours was more than double than that of the hyaluronic acid concentration. This may be due to different release kinetics or to the fact that the solidification of the gel within the round window niche, which fixed it locally, allowed for a better contact with the round window membrane. After 3 hours, parts of the much more fluid hyaluronic acid formulation may already have drained from the round window niche respectively even the middle ear space down into the pharynx.

The invention claimed is:

1. A method of treating a middle or inner ear disease comprising intratympanically administering to a patient in need thereof a controlled release composition comprising a pharmaceutically active agent and a thermosetting polymer; wherein the pharmaceutically active agent is selected from antibiotics and is suspended in the composition, and the thermosetting polymer has a gelation temperature of at least about 15° C.,
    wherein the thermosetting polymer is poloxamer 407 and is present at a concentration of about 20% (w/w), and
    wherein the antibiotic is fluoroquinolone.

2. The method of claim 1, wherein the composition provides controlled release of the pharmaceutically active agent over an extended period of time of one or more days.

3. The method of claim 1, wherein the composition further comprises a phosphate which buffers the pH of the composition to about 7.4.

4. The method of claim 1, wherein the composition is contained in a syringe optionally connected to a needle.

5. The method of claim 4, wherein a single dose of the composition in the syringe is about 200 μL to about 500 μL.

6. The method of claim 1, wherein the composition is administered by inserting it into the middle ear.

7. The method of claim 1, wherein the composition is administered by infusion, injection, or by deposition by means of a surgical instrument.

8. The method of claim 1, wherein the middle or inner ear disease is selected from the group consisting of tinnitus, hearing loss, inner ear inflammations or infections, autoimmune disorders, vertigo, and Meniere's Disease.

9. The method of claim 1, wherein the middle ear disease is a viral or a bacterial infection disease.

* * * * *